(12) United States Patent
Otero et al.

(10) Patent No.: US 10,675,038 B2
(45) Date of Patent: Jun. 9, 2020

(54) COMPOSITIONS AND DEVICES FOR THE OCCLUSION OF CAVITIES AND PASSAGEWAYS

(71) Applicants: Applied Cardiovascular Solutions, LLC, Austin, TX (US); Board of Regents, The University of Texas System, Austin, TX (US)

(72) Inventors: F. Javier Otero, Austin, TX (US); Joseph J. Beaman, Austin, TX (US); Krishnendu Roy, Marietta, GA (US); Andrew Zimbroff, Upland, CA (US)

(73) Assignees: Applied Cardiovascular Solutions, LLC, Austin, TX (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/409,266

(22) Filed: May 10, 2019

(65) Prior Publication Data
US 2019/0357915 A1 Nov. 28, 2019

Related U.S. Application Data

(63) Continuation of application No. 14/208,338, filed on Mar. 13, 2014.

(60) Provisional application No. 61/780,533, filed on Mar. 13, 2013.

(51) Int. Cl.
| | | |
|---|---|---|
| A61B 17/12 | (2006.01) | |
| A61B 17/00 | (2006.01) | |
| A61L 27/18 | (2006.01) | |
| A61B 90/00 | (2016.01) | |

(52) U.S. Cl.
CPC .... *A61B 17/12122* (2013.01); *A61B 17/1219* (2013.01); *A61B 17/12186* (2013.01); *A61L 27/18* (2013.01); *A61B 17/0057* (2013.01); *A61B 17/00491* (2013.01); *A61B 2017/00004* (2013.01); *A61B 2017/00893* (2013.01); *A61B 2017/00898* (2013.01); *A61B 2090/3966* (2016.02); *A61L 2400/06* (2013.01); *A61L 2430/36* (2013.01)

(58) Field of Classification Search
CPC .......... A61B 17/00491; A61B 17/0057; A61B 17/12186; A61B 17/12181; A61B 17/12122; A61B 17/12195; A61B 17/1219; A61B 2017/00495; A61B 2017/00575

See application file for complete search history.

(56) References Cited

U.S. PATENT DOCUMENTS

| | | | | | |
|---|---|---|---|---|---|
| 4,644,033 | A | * | 2/1987 | Gnanou | C08G 18/4833 524/590 |
| 5,116,315 | A | * | 5/1992 | Capozzi | A61B 17/00491 222/137 |
| 6,047,861 | A | * | 4/2000 | Vidal | A61B 17/00491 222/137 |

(Continued)

*Primary Examiner* — Christopher L Templeton
(74) *Attorney, Agent, or Firm* — Meunier Carlin & Curfman LLC

(57) ABSTRACT

Provided herein are methods, compositions, and devices for occluding cavities or passageways in a patient, in particular cavities or passageways in the cardiovascular system of a patient, such as the LAA of a patient's heart. The methods, compositions, and devices can be used to percutaneously occlude the LAA, decreasing the risk of thromboembolic events associated with AF.

20 Claims, 4 Drawing Sheets

(56) References Cited

U.S. PATENT DOCUMENTS

| | | | | |
|---|---|---|---|---|
| 2004/0044361 | A1* | 3/2004 | Frazier | A61B 17/0057 606/200 |
| 2004/0258754 | A1* | 12/2004 | Alakhov | A61K 9/10 424/486 |
| 2005/0245891 | A1* | 11/2005 | McCormick | A61B 17/12022 604/507 |
| 2007/0014755 | A1* | 1/2007 | Beckman | A61K 31/28 424/78.27 |
| 2008/0140106 | A1* | 6/2008 | McGrath | A61L 24/001 606/191 |
| 2008/0253987 | A1* | 10/2008 | Rehor | A61L 24/046 424/78.37 |
| 2009/0291115 | A1* | 11/2009 | Gemeinhart | A61K 9/0024 424/423 |
| 2009/0324719 | A1* | 12/2009 | Dye | A61L 15/32 424/484 |
| 2010/0191279 | A1* | 7/2010 | Kassab | A61B 17/00491 606/213 |
| 2012/0035335 | A1* | 2/2012 | Ladet | A61B 17/00491 525/445 |
| 2014/0212373 | A1* | 7/2014 | Chau | A61K 31/573 424/78.31 |

* cited by examiner

COMPOSITIONS AND DEVICES FOR THE OCCLUSION OF CAVITIES AND PASSAGEWAYS

CROSS REFERENCE TO RELATED APPLICATIONS

This application is a continuation of U.S. patent application Ser. No. 14/208,338, filed Mar. 13, 2014, which claims the benefit of U.S. Provisional Application No. 61/780,533, filed Mar. 13, 2013, the disclosures of which are herein incorporated by reference.

FIELD

The present disclosure is generally related to methods, compositions, and devices for occluding cavities or passageways in a patient, in particular cavities or passageways in the cardiovascular system of a patient, such as the left atrial appendage (LAA) of a patient's heart.

BACKGROUND

Embolic stroke is a leading cause of death and disability among adults. The most common cause of embolic stroke emanating from the heart is thrombus formation due to atrial fibrillation (AF). AF is an arrhythmia of the heart that results in a rapid and chaotic heartbeat, producing decreased cardiac output and leading to irregular and turbulent blood flow in the vascular system.

In the case of patients who exhibit AF and develop an atrial thrombus, clot formation typically occurs in the left atrial appendage (LAA) of the patient's heart. The LAA is a small cavity formed within the lateral wall of the left atrium between the mitral valve and the root of the left pulmonary vein. In normal hearts, the LAA contracts in conjunction with the rest of the left atrium during the cardiac cycle; however in the case of patients suffering from AF, the LAA often fails to contract with any vigor. As a consequence, blood can stagnate within the LAA, resulting in thrombus formation.

Elimination or containment of thrombus formed within the LAA offers the potential to significantly reduce the incidence of stroke in patients suffering from AF. Pharmacological therapies, for example the oral or systemic administration of anticoagulants such as warfarin, are often used to prevent thrombus formation. However, anticoagulant therapy is often undesirable or unsuccessful due to medication side effects (e.g., hemorrhage), interactions with foods and other drugs, and lack of patient compliance.

Invasive surgical or thorascopic techniques have been used to obliterate the LAA, however, many patients with AF are not suitable candidates for such surgical procedures due to a compromised condition or having previously undergone cardiac surgery. In addition, the perceived risks of surgical procedures often outweigh the potential benefits.

Recently, percutaneous occlusion implants for use in the LAA have been investigated as alternatives to anticoagulant therapy. However, these implants are relatively non-conforming. Due to the non-uniform shape of the LAA, existing implants cannot completely seal the opening of the LAA in all patients. As a consequence, approximately 15% of patients receiving these implants experience incomplete LAA closure, necessitating prolonged treatment with anticoagulants. The anatomy of the left atrium and LAA of some patients also precludes the use of such implants. In addition, the occlusion implants can also cause life-threatening perforations of the LAA during the placement procedure.

More effective methods of occluding cavities or passageways in a patient, in particular cavities or passageways in the cardiovascular system of a patient, such as the LAA, offer the potential to improve patient outcomes while eliminating the undesirable consequences of existing therapies.

SUMMARY

Provided are methods, compositions, and devices for occluding cavities or passageways in a patient, in particular cavities or passageways in the cardiovascular system of a patient, such as the LAA of a patient's heart. The methods, compositions, and devices can be used to decrease the rate of thromboembolic events associated with AF by occluding the LAA.

Methods for occluding the LAA of a patient can involve injecting a crosslinkable biomaterial into the LAA of the patient. The crosslinkable biomaterial can be, for example, a fluid or fluids which can comply with the irregular shape of the interior of the LAA. Upon injection, the crosslinkable biomaterial can crosslink in situ in the LAA, forming a biocompatible polymeric matrix. The biocompatible polymeric matrix can function as an occlusive body, occupying the void space of the LAA without adversely impacting cardiac function.

The crosslinkable biomaterial can be injected into the LAA percutaneously. In some embodiments, the crosslinkable biomaterial can be percutaneously injected via a delivery catheter. The delivery catheter can comprise (i) a proximal region: (ii) a distal region comprising a distal tip; (iii) at least a first lumen extending from the proximal region to the distal region; and (iv) an occluding element positioned in proximity to the distal tip. The delivery catheter can further comprise at least a second lumen extending from the proximal region to the distal region. In some embodiments, the first lumen can be fluidly isolated from the second lumen. In other embodiments, the first lumen and the second lumen are fluidly connected by a mixing channel.

The delivery catheter can be is inserted into the vasculature of the patient (e.g., into the femoral vein), and advanced through the patient's vasculature, such that the distal tip of the delivery catheter reaches the patient's left atrium. The distal tip of the delivery catheter can then be advanced into the LAA, such that the occluding element of the delivery catheter transitorily occludes the LAA. A crosslinkable biomaterial can then be injected into the LAA of the patient via the delivery catheter where it increases in viscosity upon crosslinking to form a biocompatible polymeric matrix. The crosslinkable biomaterial as well as the resultant biocompatible polymeric matrix can be selected to possess suitable materials properties (e.g., viscosity, cohesive strength, adhesive strength, elasticity, degradation rate, swelling behavior, cure time, etc.) for use in occlusion of the LAA.

In some embodiments, the crosslinkable biomaterial comprises a multicomponent composition. For example, the crosslinkable biomaterial can comprise a first precursor molecule present in a first solution and a second precursor molecule present in a second solution, wherein the first precursor molecule is reactive with the second precursor molecule to form a biocompatible polymeric matrix. In one embodiment, the two solutions are combined during the course of injection via the delivery catheter (e.g., by mixing within a mixing channel within the delivery catheter). In another embodiment, the two solutions are individually (simultaneously or sequentially) injected into the LAA, and combine in situ to form a biocompatible polymeric matrix.

DETAILED DESCRIPTION

Figure 1:
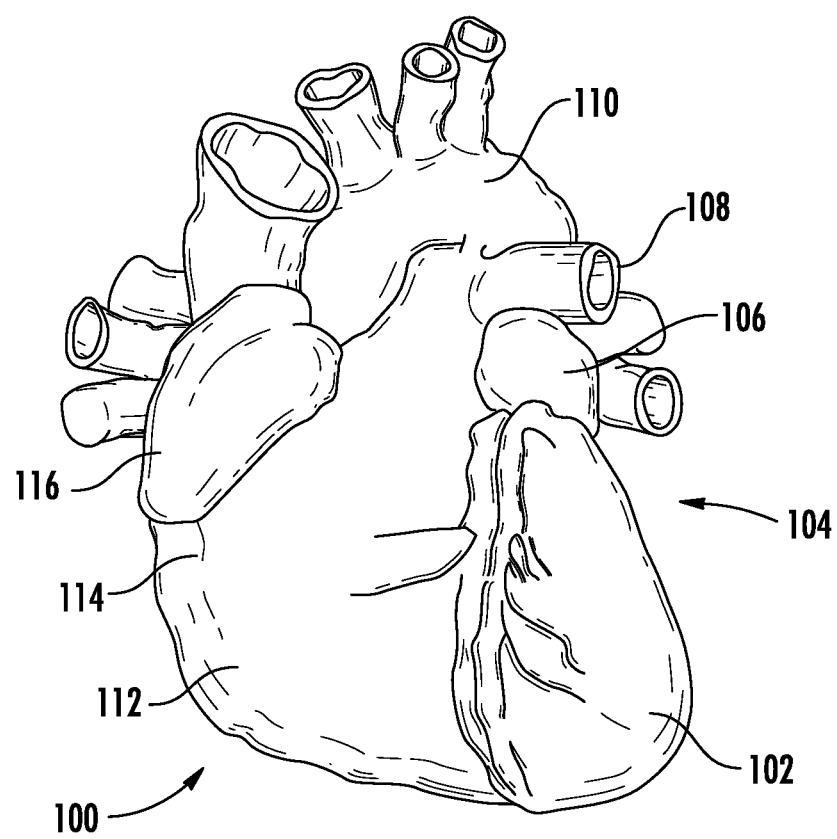
FIG. 1 is an anterior illustration of a heart, including proximal portions of the great vessels.
Figure 4:
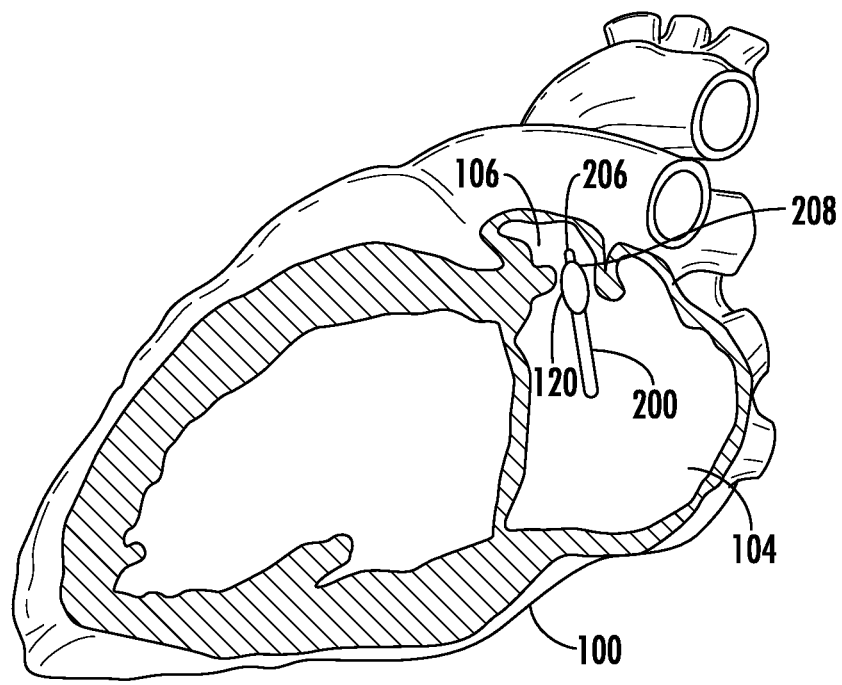
FIG. 4 is a schematic illustration of a patient's heart in partial section with a delivery catheter positioned within the opening of the LAA.

To facilitate understanding of the physiology associated with the methods, compositions, and devices described herein, FIG. 1 illustrates the anatomy of the human heart (100). Referring to FIG. 1, the heart 100 is illustrated to show certain portions including the left ventricle (102), the left atrium (104), the LAA (106), the pulmonary artery (108), the aorta (110), the right ventricle (112), the right atrium (114), and the right atrial appendage (116). The left atrium is located above the left ventricle, and is separated from the left ventricle by the mitral valve (not illustrated). As shown in FIG. 4, the LAA (106) has an irregular finger-like or windsock shape with an opening (120) approximately 1.5 cm in diameter. The LAA is normally in fluid communication with the left atrium such that blood flows in and out of the LAA as the heart beats.

Provided are methods, compositions, and devices for occluding cavities or passageways in a patient, in particular cavities or passageways in the cardiovascular system of a patient (e.g., the LAA of a patient's heart). Methods for occluding cavities or passageways in a patient, such as the LAA, can involve injecting or otherwise introducing a crosslinkable biomaterial into the cavity or passageway. Any suitable biomaterial can be used. For example, the biomaterial can be a crosslinkable biomaterial which is injected into the cavity or passageway (e.g., the LAA) in a fluid or gel form, and which crosslinks in situ, increasing in viscosity to form a biocompatible polymeric matrix. In these cases, the biocompatible polymeric matrix can function as an occlusive body, occupying the void space of the cavity or passageway. In the case of injection of a crosslinkable biomaterial into the LAA for purposes of occlusion, the biocompatible polymeric matrix can function as an occlusive body, occupying the void space of the LAA without adversely impacting cardiac function.

In situ formation, as generally used herein, refers to the ability of precursor molecules that are substantially uncrosslinked prior to and at the time of injection into a patient to crosslink by forming covalent and/or non-covalent linkages with each other at the site of injection in the body of the patient.

The crosslinkable biomaterial as well as the resultant biocompatible polymeric matrix can be selected to possess suitable materials properties (e.g., viscosity, cohesive strength, adhesive strength, elasticity, degradation rate, swelling behavior, cure time, etc.) for use in occlusion of a particular cavity or passageway, such as the LAA.

For example, the biocompatible polymeric matrix can exhibit an equilibrium swelling ratio suitable for occlusion of the LAA. Swelling refers to the uptake of water or biological fluids by the biocompatible polymeric matrix. The swelling of the biocompatible polymeric matrix can be quantified using the equilibrium swelling ratio, defined as the mass of the biocompatible polymeric matrix at equilibrium swelling (i.e., the materials maximum swollen weight) divided by the mass of the biocompatible polymeric matrix prior to swelling (e.g., immediately following curing). In many cases, equilibrium swelling is reached within a relatively short period of time (e.g., within about 24-48 hours).

In some embodiments, the biocompatible polymeric matrix exhibits an equilibrium swelling ratio of less than about 8 (e.g., less than about 7.5, less than about 7.0, less than about 6.5, less than about 6.0, less than about 5.5, less than about 5.0, less than about 4.5, less than about 4.0, less than about 3.5, less than about 3.0, less than about 2.5, less than about 2.0, less than about 1.5, less than about 1.0, or less than about 0.5). In some embodiments, the biocompatible polymeric matrix exhibits an equilibrium swelling ratio of greater than 0 (e.g., greater than about 0.5, greater than about 1.0, greater than about 1.5, greater than about 2.0, greater than about 2.5, greater than about 3.0, greater than about 3.5, greater than about 4.0, greater than about 4.5, greater than about 5.0, greater than about 5.5, greater than about 6.0, greater than about 6.5, greater than about 7.0, or greater than about 7.5).

The biocompatible polymeric matrix can exhibit an equilibrium swelling ratio ranging from any of the minimum values described above to any of the maximum values described above. For example, the biocompatible polymeric matrix can exhibit an equilibrium swelling ratio of from greater than 0 to about 8.0 (e.g., from about 2.0 to about 8.0, of from about 2.5 to about 6.0).

The biocompatible polymeric matrix can have mechanical properties that are compatible with cardiac function, such that the presence of the biocompatible polymeric matrix within the LAA does not substantially impede or inhibit cardiac function. For example, the biocompatible polymeric matrix can be formed to be at least partially compliant with the constrictive action of the heart muscle throughout the cardiac cycle. Suitable biocompatible polymeric matrices can have elastic moduli ranging from about 0.01 to about 100 kPa.

In some cases, biocompatible polymeric matrix is formed to have an elastic modulus similar to that of cardiac tissue. In some embodiments, the biocompatible polymeric matrix has an elastic modulus greater than about 5 kPa (e.g., greater than about 6 kPa, greater than about 7 kPa, greater than about 8 kPa, greater than about 9 kPa, greater than about 10 kPa, greater than about 11 kPa, greater than about 12 kPa, greater than about 13 kPa, greater than about 14 kPa, greater than about 15 kPa, greater than about 16 kPa, greater than about 17 kPa, greater than about 18 kPa, or greater than about 19 kPa. In some embodiments, the biocompatible polymeric matrix has an elastic modulus of less than about 20 kPa (e.g., less than about 19 kPa, less than about 18 kPa, less than about 17 kPa, less than about 16 kPa, less than about 15 kPa, less than about 14 kPa, less than about 13 kPa, less than about 12 kPa, less than about 11 kPa, less than about 10 kPa, less than about 9 kPa, less than about 8 kPa, less than about 7 kPa, or less than about 6 kPa).

The biocompatible polymeric matrix can have an elastic modulus ranging from any of the minimum values described above to any of the maximum values described above. For example, the biocompatible polymeric matrix can have an elastic modulus of from about 5 kPa to about 20 kPa (e.g., from about 9 kPa to about 17 kPa, from about 10 kPa to about 15 kPa, or from about 8 kPa to about 12 kPa).

The biocompatible polymeric matrix can have a cohesive strength suitable for occlusion of the LAA. Cohesive strength (also referred to as burst strength) refers to the ability of the biocompatible polymeric matrix to remain intact (i.e., not rupture, tear or crack) when subjected to physical stresses or environmental conditions. The cohesive strength of the biocompatible polymeric matrix can be measured using methods known in the art, for example, using the standard methods described in ASTM F-2392-04 (standard test for the burst strength of surgical sealants). In some embodiments, the biocompatible polymeric matrix has a cohesive strength effective such that the biocompatible polymeric matrix remains intact (e.g., does not fragment or break apart into smaller pieces which exit the LAA) for a period of time effective to permit the LAA to be sealed via endothelialization prior to fragmentation of the biocompatible polymeric matrix.

The biocompatible polymeric matrix can also have a viscosity which minimizes migration of biocompatible polymeric matrix out of the LAA following injection. In some embodiments, the biocompatible polymeric matrix has a viscosity of at least 50,000 cP (e.g., at least 60,000 cP, at least 70.000 cP, at least 75,000 cP, at least 80,000 cP, at least 90,000 cP, at least 100,000 cP, or more) at body temperature (e.g., at 37° C.).

The biocompatible matrix can also be selected such that is it retained at the site of occlusion (e.g., inside the LAA) by a combination of adhesion to the tissues at the site of occlusion and mechanical interaction with the anatomy at the site of occlusion. For example, the biocompatible polymeric matrix can have an adhesive strength suitable for occlusion of the LAA. Adhesive strength refers to the ability of the biocompatible polymeric matrix to remain attached to the tissues at the site of administration (e.g., the interior of the LAA) when subjected to physical stresses or environmental conditions. In some embodiments, the biocompatible polymeric matrix has an adhesive strength effective such that the biocompatible polymeric matrix remains within the LAA (e.g., does not exit the LAA) for a period of time effective to permit the LAA to be sealed via endothelialization prior to fragmentation of the biocompatible polymeric matrix. Mechanical forces, governed by a combination of properties which can include the swelling of the biocompatible polymeric matrix, the local anatomy at the site of injection (e.g., the particular 3-dimensional shape of the LAA and/or the surface texture of the LAA interior), and the friction of the biocompatible polymeric matrix against tissue at the site of injection, can also contribute to retention of the biocompatible matrix at the site of injection.

The biocompatible polymeric matrix can be formed from materials which support (i.e., do not inhibit) endothelialization. Endothelialization refers to the growth and/or proliferation of endothelial cells on a surface, such as the blood-contacting surface, of the biocompatible polymeric matrix. These materials can be biodegradable or non-biodegradable. A biodegradable material is one which decomposes under normal in vivo physiological conditions into components which can be metabolized or excreted.

In some cases, the biocompatible polymeric matrix can be biodegradable. When the biocompatible polymeric matrix is biodegradable, the biocompatible polymeric matrix can have a degradation rate effective to permit the LAA to be sealed via endothelialization prior to erosion of the biocompatible polymeric matrix. For example, the biocompatible polymeric matrix can have a degradation rate effective to permit the LAA to be sealed via endothelialization prior to erosion of 25% by volume of the biocompatible polymeric matrix from the LAA (e.g., prior to erosion of 20% by volume of the biocompatible polymeric matrix from the LAA, prior to erosion of 15% by volume of the biocompatible polymeric matrix from the LAA, prior to erosion of 10% by volume of the biocompatible polymeric matrix from the LAA, or prior to erosion of 5% by volume of the biocompatible polymeric matrix from the LAA).

In some embodiments, the biocompatible polymeric matrix has a degradation rate such that about 70% or less by weight of the biocompatible polymeric matrix degrades within 90 days of curing, as measured using the standard method described in Example 1 (e.g., about 60% or less by weight, about 55% or less by weight, about 50%6 or less by weight, about 45% or less by weight, about 40% or less by weight, or less). In some embodiments, the biocompatible polymeric matrix has a degradation rate such that about 85% or less by weight of the biocompatible polymeric matrix degrades within 120 days of curing, as measured using the standard method described in Example 1 (e.g., about 80% or less by weight, about 75% or less by weight, about 70% or less by weight, about 65% or less by weight, about 60% or less by weight, about 55% or less by weight, about 50% or less by weight, or less).

In one embodiment, the biocompatible polymeric matrix has a degradation rate such that about 45% or less by weight of the biocompatible polymeric matrix degrades within 90 days of curing, and about 55% or less by weight of the biocompatible polymeric matrix degrades within 120 days of curing, as measured using the standard method described in Example 1

Suitable biocompatible polymeric matrices can be formed from a variety of natural and/or synthetic materials. In certain embodiments, the biocompatible polymeric matrix is a hydrogel. Hydrogels are water-swellable materials formed from oligomeric or polymeric molecules which are cross-linked to form a three dimensional network. Hydrogels can be designed to form in situ (for example, from injectable precursors which crosslink in vivo). As gels, these materials can exhibit properties characteristic of both liquids (e.g., their shape can be resilient and deformable) and solids (e.g., their shape can be discrete enough to maintain three dimensions on a two dimensional surface).

The crosslinkable biomaterial can be designed to rapidly cure in situ upon injection. In some embodiments, the crosslinkable biomaterial has a cure time, as measured using the standard method described in Example 1, of less than about 20 minutes (e.g., less than about 15 minutes, less than about 10 minutes, less than about 5 minutes, less than about 3 minutes, or less than about 1 minute).

The crosslinkable biomaterial injected into the LAA can have a low viscosity relative to the biocompatible polymeric matrix. This can allow the crosslinkable biomaterial to be readily injected, for example, via a hand-powered delivery device such as a syringe. This can provide a physician with a large degree of control over the flow rate of the crosslinkable biomaterial during injection, and allow the flow to be altered or stopped, as required, during the course of injection. The relatively low viscosity of the crosslinkable biomaterial relative to the biocompatible polymeric matrix also can allow the crosslinkable biomaterial to conform to the shape of the LAA prior to curing.

For example, in some embodiments, the crosslinkable biomaterial injected into the LAA has a viscosity of about 1,000 cP or less (e.g., about 900 cP or less, about 800 cP or less, about 750 cP or less, about 700 cP or less, about 600 cP or less, about 500 cP or less, about 400 cP or less, about 300 cP or less, about 250 cP or less, about 200 cP or less, about 150 cP or less, about 100 cP or less, or, about 50 cP or less). In certain cases, the crosslinkable biomaterial injected into the LAA has a viscosity of at least 1 cP (e.g., at least 2 cP, at least 2.5 cP, at least 5 cP, or at least 10 cP). The crosslinkable biomaterial can have a viscosity ranging from any of the minimum values described above to any of the maximum values described above.

In some embodiments, the crosslinkable biomaterial comprises a multicomponent composition which crosslinks in situ to form a biocompatible polymeric matrix. For example, the crosslinkable biomaterial can comprise a first precursor molecule and a second precursor molecule. "Precursor molecule", as used herein, generally refers to a molecule present in the crosslinkable biomaterial which interacts with (e.g., crosslinks with) other precursor molecules of the same or different chemical composition in the crosslinkable biomaterial to form a biocompatible polymeric matrix. Precursor molecules can include monomers, oligomers and polymers which can be crosslinked covalently and/or non-covalently.

The multiple components of the composition (e.g., the first precursor molecule and the second precursor molecule) can be combined prior to injection, can be present in two or more separate solutions which are combined during the injection (e.g., by mixing within a delivery device used to inject the material), or can be present in two or more separate solutions which are individually injected into the LAA.

In some embodiments, the crosslinkable biomaterial comprises a first precursor molecule present in a first solution and a second precursor molecule present in a second solution. In one embodiment, the two solutions are combined during the course of injection (e.g., by mixing within a delivery device used to inject the material). In another embodiment, the two solutions are individually injected into the LAA, and combine in situ. In these cases, the two solutions can be injected simultaneously or sequentially. Depending on the mechanism of crosslinking, an accelerator (e.g., a pH modifying agent or radical initiator) can be added and/or an external stimulus (e.g., UV irradiation) can be applied to ensure uniform and rapid curing of the crosslinkable biomaterial to form a biocompatible matrix. In cases where an accelerator is added, the accelerator can be incorporated into one or more of the solutions containing a precursor molecule prior to injection. The accelerator can also be present in a solution which does not contain a precursor molecule. This accelerator solution can then be injected simultaneously or sequentially with one or more solutions containing one or more precursor compounds to initiate formation of the biocompatible polymeric matrix.

Suitable precursor molecules can be selected in view of the desired properties of the crosslinkable biomaterial and resultant biocompatible polymeric matrix. In some cases, the crosslinkable biomaterial comprises one or more oligomeric or polymeric precursor molecules. For example, precursor molecules can include, but are not limited to, polyether derivatives, such as poly(alkylene oxide)s or derivatives thereof, polysaccharides, peptides, and polypeptides, poly (vinyl pyrrolidinone) ("PVP"), poly(amino acids), and copolymers thereof.

The precursor molecules can further comprise one or more reactive groups. Reactive groups are chemical moieties in a precursor molecule which are reactive with a moiety (such as a reactive group) present in another precursor molecule to form one or more covalent and/or non-covalent bonds. Examples of suitable reactive groups include, but are not limited to, active esters, active carbonates, aldehydes, isocyanates, isothiocyanates, epoxides, alcohols, amines, thiols, maleimides, groups containing one or more unsaturaturated C—C bonds (e.g., alkynes, vinyl groups, vinylsulfones, acryl groups, methacryl groups, etc.), azides, hydrazides, dithiopyridines, N-succinimidyl, and iodoacetamides. Suitable reactive groups can be incorporated in precursor molecules to provide for crosslinking of the precursor molecules.

In some embodiments, one or more of the precursor molecules comprises a poly(alkylene oxide)-based oligomer or polymer. Poly(alkylene oxide)-based oligomer and polymers are known in the art, and include polyethylene glycol ("PEG"), polypropylene oxide ("PPO"), polyethylene oxide-co-polypropylene oxide ("PEO-PPO"), co-polyethylene oxide block or random copolymers, poloxamers, meroxapols, poloxamines, and polyvinyl alcohol ("PVA"). Block copolymers or homopolymers (when A=B) may be linear (AB, ABA, ABABA or ABCBA type), star ($A_nB$ or $BA_nC$, where B is at least n-valent, and n is an integer of from 3 to 6) or branched (multiple A's depending from one B). In certain embodiments, the poly(alkylene oxide)-based oligomer or polymer comprises PEG, a PEO-PPO block copolymer, or combinations thereof.

In some embodiments, one or more of the precursor molecules is defined by Formula I or Formula II

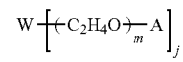

Formula I

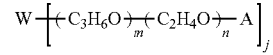

Formula II wherein
W is a branch point;
A is a reactive group (e.g., a nucleophilic group or a conjugated unsaturated group);
m and n are integers of from 1 to 500 (e.g., an integers of from 1 to 200); and
j is an integer greater than 2 (e.g., an integer of from 2 to 8).

In some embodiments, one or more of the precursor molecules comprises a biomacromolecule. The biomacromolecule can be, for example, a protein (e.g., collagen) or a polysaccharide. Examples of suitable polysaccharides include cellulose and derivatives thereof, dextran and derivatives thereof, hyaluronic acid and derivatives thereof, chitosan and derivatives thereof, alginates and derivatives thereof, and starch or derivatives thereof. Polysaccharides can derivatized by methods known in art. For example, the polysaccharide backbone can be modified to influence polysaccharide solubility, hydrophobicityhydrophilicity, and the properties of the resultant biocompatible polymeric matrix formed from the polysaccharide (e.g., matrix degradation time). In certain embodiments, one or more of the precursor molecules comprises a biomacromolecule (e.g., a polysaccharide) which is substituted by two or more (e.g., from about 2 to about 100, from about 2 to about 25, or from about 2 to about 15) reactive groups (e.g., a nucleophilic group or a conjugated unsaturated group).

In some cases, the crosslinkable biomaterial can comprise a first precursor molecule which comprises an oligomer or polymer having one or more first reactive groups, each first reactive group comprising one or more pi bonds, and a second precursor molecule comprises an oligomer or polymer having one or more second reactive groups, each second reactive group comprising one or more pi bonds. The first reactive group can be reactive (e.g., via a Click chemistry reaction) with the second reactive group, so as to form a covalent bond between the first precursor molecule and the second precursor molecule. For example, the first reactive group and the second reactive group undergo a cycloaddition reaction, such as a [3+2] cycloaddition (e.g., a Huisgen-type 1,3-dipolar cycloaddition between an alkyne and an azide) or a Diels-Alder reaction.

In some cases, the crosslinkable biomaterial can comprise a first precursor molecule which comprises an oligomer or polymer having one or more nucleophilic groups (e.g. amino groups, thiol groups hydroxy groups, or combinations thereof), and a second precursor molecule which comprises an oligomer or polymer having one or more conjugated unsaturated groups (e.g., vinyl sulfone groups, acryl groups, or combinations thereof). In such cases, the first precursor molecule and the second precursor molecule can react via a Michael-type addition reaction. Suitable conjugated unsaturated groups are known in the art, and include those moieties described in, for example, U.S. Patent Application Publication No. US 2008/0253987 to Rehor, et al., which is incorporated herein by reference in its entirety.

In certain embodiments, the crosslinkable biomaterial can comprise a first precursor molecule and a second precursor molecule. The first precursor molecule comprises a poly(alkylene oxide)-based oligomer or polymer having x nucleophilic groups, wherein x is an integer greater than or equal to 2 (e.g., an integer of from 2 to 8, or an integer of from 2 to 6). The poly(alkylene oxide)-based polymer can comprise, for example, poly(ethylene glycol). The nucleophilic groups can be selected from the group consisting of sulfhydryl groups and amino groups. The first precursor molecule can have a molecular weight of from about 1 kDa to about 10 kDa (e.g., from about 1 kDa to about 5 kDa). In some embodiments, the first precursor molecule comprises pentaerythritol poly(ethylene glycol)ether tetrasulfhydryl.

The second precursor molecule can comprises a biomacromolecule having y conjugated unsaturated groups, wherein y is an integer greater than or equal to 2 (e.g. an integer of from 2 to 100, or an integer of from 2 to 25). The biomacromolecule can comprise a polysaccharide, such as dextran, hyaluronic acid, chitosan, alginate, or derivatives thereof. The conjugated unsaturated groups can be selected from the group consisting of vinyl sulfone groups and acryl groups. The second precursor molecule can have a molecular weight of from about 2 kDa to about 250 kDa (e.g., from about 5 kDa to about 50 kDa). In some embodiments, the second precursor molecule comprises dextran vinyl sulfone.

In some embodiments, the in situ crosslinking of the precursor molecules takes place under basic conditions. In these embodiments, the crosslinkable biomaterial can further include a base to activate the crosslinking of the precursor molecules. A variety of bases comply with the requirements of catalyzing, for example, Michael addition reactions under physiological conditions without being detrimental to the patient's body. Suitable bases include, but are not limited to, tertiary alkyl-amines, such as tributylamine, triethylamine, ethyldiisopropylamine, or N,N-dimethylbutylamine. For a given composition (and mainly dependent on the type of precursor molecules), the gelation time can be dependant on the type of base and of the pH of the solution. Thus, the gelation time of the composition can be controlled and adjusted to the desired application by varying the pH of the basic solution.

In a some embodiments, the base, as the activator of the covalent crosslinking reaction, is selected from aqueous buffer solutions which have their pH and pK value in the same range. The pK range can be between 9 and 13. Suitable buffers include, but are not limited to, sodium carbonate, sodium borate and glycine. In one embodiment, the base is sodium carbonate.

The crosslinkable biomaterial can further contain organic and/or inorganic additives, such as thixotropic agents, stabilizers for stabilization of the precursor molecules in order to avoid premature crosslinking, and/or fillers which can result in an increase or improvement in the mechanical properties (e.g., cohesive strength and/or elastic modulus) of the resultant biocompatible matrix. Examples of stabilizing agents include radical scavengers, such as butylated hydroxytoluene or dithiothreitol.

In some embodiments, a bioactive agent can be incorporated into the crosslinkable biomaterial (and thus into the resultant biocompatible polymer matrix). The bioactive agent can be a therapeutic agent, prophylactic agent, diagnostic agent, or combinations thereof. In some cases, the crosslinkable biomaterial (and thus the resultant biocompatible polymer matrix) comprises an agent that promotes infiltration of cells onto or into the biocompatible polymeric matrix. For example, the agent can be an agent that promotes endothelialization. Promoting endothelialization refers to promoting, enhancing, facilitating, or otherwise increasing the attachment of, and growth of, endothelial cells on a surface of the biocompatible polymeric matrix. Examples of suitable agents that promote endothelialization are known in the art, and include growth factors (e.g., VEGF, PDGF, FGF, P1GF and combinations thereof), extracellular matrix proteins (e.g., collagen), and fibrin. In some cases, the crosslinkable biomaterial (and thus the resultant biocompatible polymer matrix) comprises an anticoagulant, such as warfarin or heparin. In these cases, the anticoagulant can be locally delivered by elution from the resultant biocompatible polymer matrix. In some cases, the crosslinkable biomaterial (and thus the resultant biocompatible polymer matrix) comprises a contrast agent, such as gold, platinum, tantalum, bismuth, or combinations thereof to facilitate imaging of the crosslinkable biomaterial (e.g., during injection) or the resultant biocompatible polymer matrix (e.g., to confirm complete occlusion of the LAA or monitor degradation of the biocompatible polymer matrix).

The crosslinkable biomaterial can be injected into the LAA percutaneously. In some embodiments, the crosslinkable biomaterial can be percutaneously injected via a delivery catheter. The particular components and features of the deliver catheter can vary based on a number of factors, including the nature of the crosslinkable biomaterial to be delivered. For example, the number of lumens in the delivery catheter and/or the presence or absence of a mixing channel can be selected in view of the identity of the precursor molecule(s) and/or the mechanism by which the biomaterial crosslinks.

Figure 2:
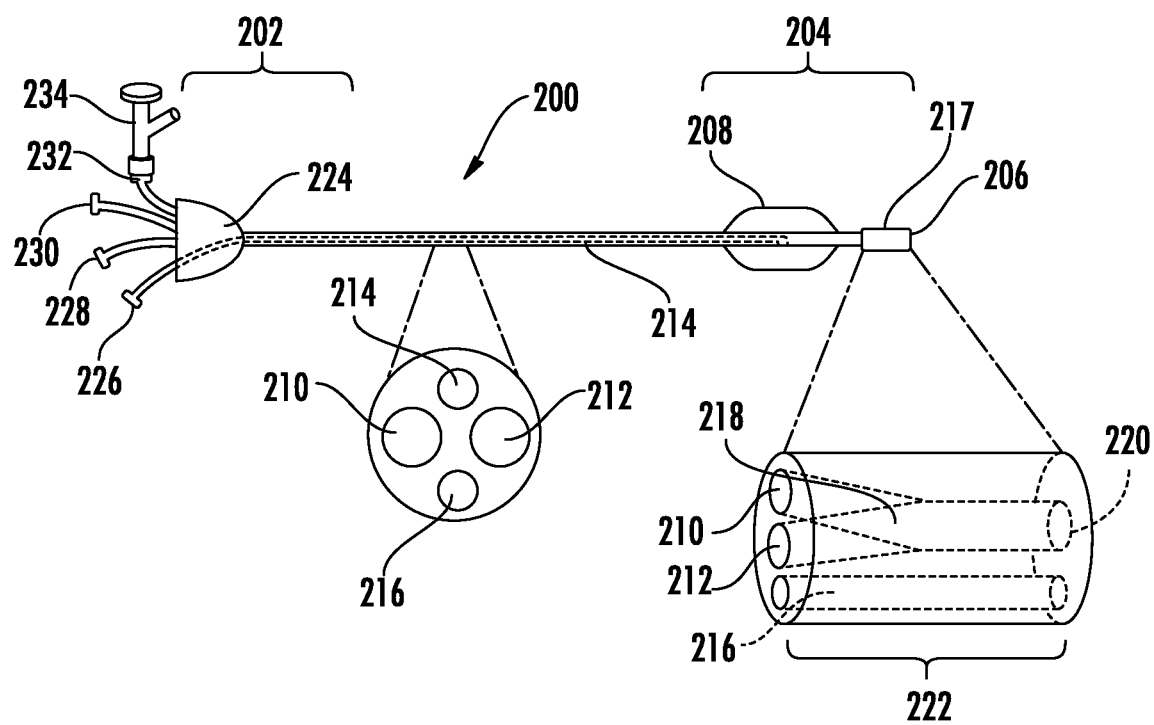
FIG. 2 is a schematic drawing illustrating a delivery catheter.

An example delivery catheter is illustrated in FIG. 2. The delivery catheter (200) can comprise a proximal region (202), a distal region (204) comprising a distal tip (206), at least a first lumen (210) extending from the proximal region (202) to the distal region (204), and an occluding element (208) positioned in proximity to the distal tip (206).

The delivery catheter can be structured to accommodate the anatomy of a patient, in terms of its dimensions (e.g., length and cross-sectional dimensions), configurations, and operability, so as to facilitate percutaneous delivery of the crosslinkable biomaterial to the cavity or passageway to be occluded. For example, in the case of a delivery catheter configured to deliver a crosslinkable biomaterial to the LAA of a patient, the dimensions (e.g., length and cross-sectional dimensions), configurations, and operability of the delivery catheter can be designed to accommodate the vascular geometry of a patient.

The cross-sectional dimension (e.g., the diameter or thickness) of the delivery catheter can be configured to accommodate the natural interior dimensions of vasculature of a patient, so as to permit advancement of the delivery catheter through the patient's vasculature to reach the LAA. In some cases, the largest cross-sectional dimension of the portion of the catheter which is configured to be advanced within the patient's vasculature is about 5.0 mm or less (e.g., about 4.7 mm or less, about 4.3 mm or less, about 4.0 mm or less, about 3.7 mm or less, about 3.3 mm or less, about 3.0 mm or less, about 2.7 mm or less, about 2.3 mm or less, or about 2.0 mm or less, about 2.5 mm or less, about 2 mm or less). The largest cross-sectional dimension of the elongate member can be at least about 1.0 mm (e.g., at least about 1.33 mm, at least about 1.67 mm, at least about 2.0 mm, at least about 2.3 mm, at least or at least about 3.0 mm). These dimensions are provided with the proviso that the cross-sectional dimensions and composition of the delivery are selected such that the structural integrity of the delivery catheter required for functionality is not substantially compromised by the cross-sectional dimensions of the delivery catheter.

The largest cross-sectional dimension of the elongate member can range from any of the minimum dimensions described above to any of the maximum dimensions described above. In some embodiments, the largest cross-sectional dimension of the elongate member is from about 1.0 mm to about 3.3 mm.

For use in methods of occluding the LAA of a patient, the delivery catheter is generally of sufficient length to reach the LAA of a patient when inserted percutaneously. For example, the delivery catheter can be long enough such that when the delivery catheter is inserted into the femoral vein of a patient, the distal tip of the delivery catheter can reach the LAA of the patient while portions of the delivery catheter proximal to the distal tip extend through the patient's vasculature to a point outside of the patient's body. In this way, the some or all of the proximal region of the delivery catheter can remain externally accessible to provide a means of manipulating the delivery catheter (e.g., advancing and retracting the delivery catheter, actuating the occluding member, etc.) and/or injecting the crosslinkable biomaterial. In certain embodiments, the delivery catheter has a length of from about 80 cm to about 130 cm (e.g., from about 90 cm to about 120 cm, or from about 100 cm to about 110 cm).

The delivery catheter, or regions thereof, can be formed from a variety of materials. The materials can optionally be selected such that the delivery catheter has structural integrity sufficient to permit advancement of the delivery catheter to the occlusion site in the patient and permit maneuvering and operation of the delivery catheter, while also permitting yielding and bending in response to encountered anatomical barriers and obstacles within the patient's body (e.g., within the vasculature).

The delivery catheter can be formed from a material or combination of materials, such as polymers, metals, and polymer-metal composites. In some examples, soft durometer materials are used to form all or part of the delivery catheter to reduce subject patient discomfort and minimize the risk of damage to the patient's vasculature (e.g., perforation). In some embodiments, the delivery catheter is formed, in whole or in part, from a polymeric material. Examples of suitable plastics and polymeric materials include, but are not limited to, silastic materials and silicon-based polymers, polyether block amides (e.g., PEBAX®, commercially available from Arkema, Colombes, France), polyimides, polyurethanes, polyamides (e.g., Nylon 6,6), polyvinylchlorides, polyesters (e.g., HYTREL®, commercially available from DuPont, Wilmington, Del.), polyethylenes (PE), polyether ether ketone (PEEK), fluoropolymers such as polytetrafluoroethylene (PTFE), perfluoroalkoxy, fluorinated ethylene propylene, or blends and copolymers thereof. Examples of suitable metals which may form some or all of the delivery catheter include stainless steel (e.g., 304 stainless steel), nickel and nickel alloys (e.g., nitinol or MP-35N), titanium, titanium alloys, and cobalt alloys. In certain embodiments, the delivery catheter comprises of two different materials. Radiopaque alloys, such as platinum and titanium alloys, may also be used to fabricate, in whole or in part, the delivery catheter to facilitate real-time imaging during procedures performed using the delivery catheter.

If desired, the delivery catheter can be coated or treated with various polymers or other compounds in order to provide desired handling or performance characteristics, such as to increase lubricity. In certain embodiments, the delivery catheter is coated with polytetrafluoroethylene (PTFE) or a hydrophilic polymer coating, such as poly (caprolactone), to enhance lubricity and impart desirable handling characteristics.

The occluding element (208) can be any structure configured to transitorially occlude the LAA when positioned in proximity to the opening of the LAA. The occluding element can be configured to be retractable or inflatable, such that the occluding element can possess a retracted or un-inflated state in which it is not configured to occlude the LAA and a deployed or inflated state in which it is configured to occlude the LAA when positioned in proximity to the opening of the LAA (e.g., to fluidly isolate the LAA from the left atrium). In some embodiments, the occluding element has a cross-sectional dimension of at least about 1.0 cm (e.g., at least about 1.25 cm, or at least about 1.5 cm) when configured to occlude the LAA (e.g., when deployed or inflated).

In some embodiments, the occluding element comprises an inflatable balloon configured to substantially seal the LAA when inflated. The inflatable balloon can be formed from any suitable fluid impermeable polymer film, and can be configured to be either compliant or non-compliant when inflated. Suitable polymeric materials that can be used to form the inflatable balloon include, for example, silicone, polyethylene, polyurethane, and PET. The inflatable balloon can include rib members extending longitudinally from its distal end to its proximal end which can be configured to provided structural integrity to the inflatable member and/or mechanically interlock with the trebeculae of the inside surface of the LAA or other surface irregularities of the inside surface of a patient's body cavity or passageway. The rib members can be disposed around the complete circumference of the inflatable balloon. The rib members can also be disposed around a portion of the circumference of the inflatable balloon. The rib members can also be disposed in a spiral configuration, or in a random orientation with respect to one another.

The inflatable balloon can be filled with a fluid or gel which can be injected under pressure through the delivery catheter and into the interior of the inflatable balloon. Accordingly, referring again to FIG. 2, the delivery catheter (200) can further comprise one or more additional lumens (e.g., one or more inflator lumens; 214) which distally extend from the proximal region (202), and are fluidly connected to the inflatable balloon. Suitable fluids to inject can include saline and silicone. The fluid, gel or polymer used to fill the inflatable balloon can contain contrast agents such as gold, tantalum, bismuth, barium sulfate or the like in order to improve, for example, visualization under flouroscopy or x-ray imaging.

Referring again to FIG. 2, the occluding element (208) can positioned within the distal region (204) of the delivery catheter in proximity to the distal tip (206), such that when the distal tip is advanced into the LAA of the patient, the occluding element configured to seal the opening the LAA. For example, is some embodiments, the occluding element (208) can be positioned within about 10 mm of the distal tip (206; measured as the distance between the distal tip and the distal end of the occluding element) of the delivery catheter (e.g., within about 9 mm, within about 8 mm, within about 7.5 mm, within about 7 mm, within about 6 mm, within about 5 mm, within about 4 mm, within about 3 mm, within about 2.5 mm, or within about 2 mm). In some embodiments, the distal region (204) of the catheter configured to be present within the left atrium can be curved to accommodate the anatomy of the LAA.

Referring again to FIG. 2, the delivery catheter (200) can further comprise a second lumen (212) extending from the proximal region (202) to the distal region (204). In some embodiments, the first lumen (210) can be fluidly isolated from the second lumen (212). In these embodiments, both the first lumen (210) and the second lumen (212) can be fluidly connected to the distal tip of the delivery catheter (206). In other embodiments, the first lumen (210) and the second lumen (212) are fluidly connected by a mixing channel (217).

The mixing channel can be configured to mix two solutions flowing through the first lumen and the second lumen, for example, so as to form a homogenous solution or suspension. As shown in FIG. 2, the mixing channel (217) can comprises a proximal end (218) fluidly connected the first lumen (210) and the second lumen (212), a distal end (220) fluidly connected to the distal tip (206) of delivery catheter; and a mixer (222) fluidly connecting the proximal end (218) and the distal end (220). The mixing channel (217) can be positioned at any suitable point along the length of the delivery catheter. In some embodiments, the mixing channel (217) is positioned within the distal region (204) of the delivery catheter (200).

Figure 3:
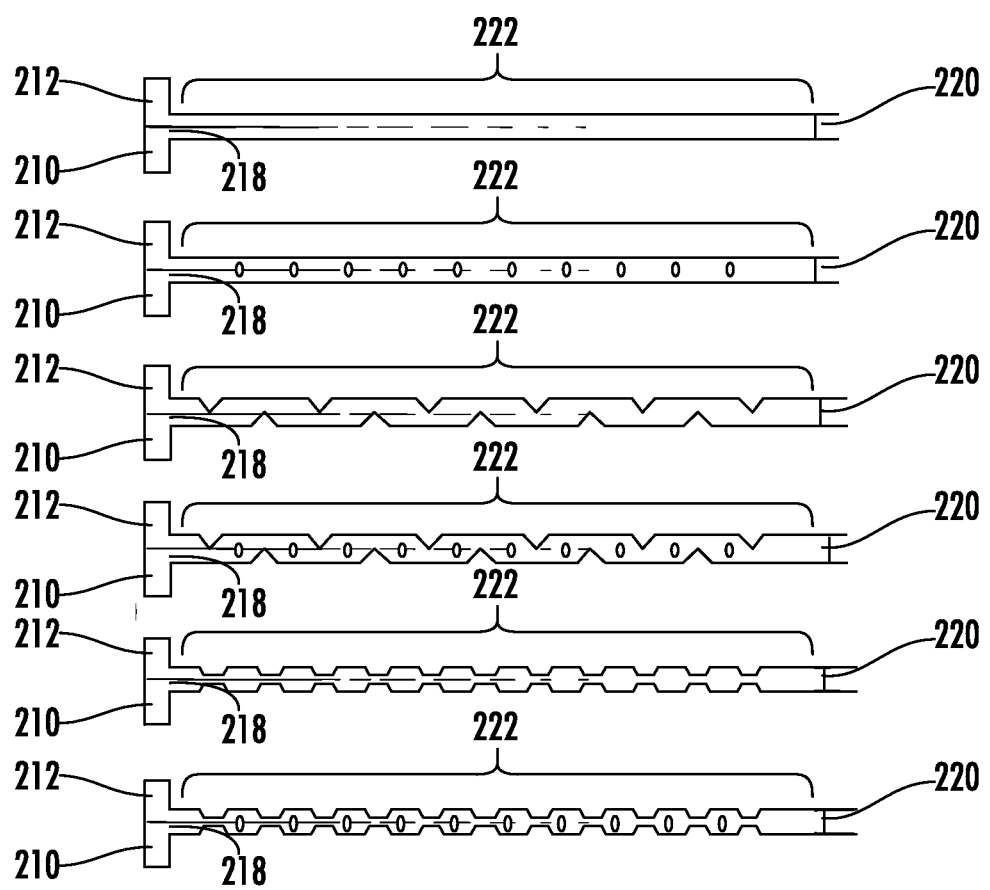
FIG. 3 is a schematic illustration of mixing channels that can be incorporated into the delivery catheter.

The mixer (222) can be one or more fluid channels configured to mix two solutions flowing into the mixer from the first lumen and the second lumen. The mixer can adopt a variety of geometries, based on for example the solutions to be mixed and the length of the mixer. For example, the mixer can be configured to mix (e.g., to render homogeneous) two solutions with Reynolds numbers of from 2 to 10 (e.g., from 3 to 5) which flow through the mixer. The mixer can be, for example, a channel (e.g., a serpentine or tortuous channel, or a channel containing one or more protrusions) which induces turbulent flow so as to mix the fluids. Suitable geometries for mixers are known in the art, and some representative geometries are illustrated for example in FIG. 3.

Referring again to FIG. 2, the delivery catheter (200) can further comprise one or more additional features. The delivery catheter (200) can further comprise one or more additional lumens (e.g., one or more auxiliary lumens; 216) which distally extend from the proximal region (202) to the distal region (204). In some embodiments, the delivery catheter (200) comprises an auxiliary lumen (216) that is fluidly connected to the distal tip (206), such that the auxiliary lumen (216) is in fluid communication with the region distal to the distal tip of the delivery catheter. The auxiliary lumen (216) can be configured to accept a guidewire and/or sheath to facilitate advancement of the delivery catheter, to accept a needle used to pierce for example the fossa ovalis to gain access to the left atrium, to accept a probe to monitor pressures distal to the distal tip of the delivery catheter, to accept a device, such as a fiber optic bundle (e.g., for transmitting UV light), configured to accelerate curing of the crosslinkable biomaterial, and/or configured to permit removal of fluid or other materials from the region distal to the distal tip of the delivery catheter.

Referring again to FIG. 2, the proximal region (202) of the delivery catheter (200) can include a manifold (224) to facilitate access to the lumens of the delivery catheter. The delivery catheter (200) can include a port for fluid connection to the one or more inflator lumens (214), a port for fluid connection to the first lumen (228), a port for fluid connection to the second lumen (230), and/or a port for fluid connection to the one or more auxiliary lumens (232). In some embodiments, one or more of the ports, such as the port for fluid connection to the one or more auxiliary lumens (232), can be connected to a branched port (e.g., a hemostatic valve; 234) to facilitate access of the lumen by multiple devices or for multiple purposes (e.g., to advance a guidewire and monitor pressure). The ports can be configured to form leak-free connections (e.g., a Luer Taper connection such as a Luer-lock or Luer-slip connection) with, for example, indeflators and syringes used to inject fluid into the lumens or to withdraw fluid from the lumens (e.g., to actuate the occluding member, to inject the crosslinkable biomaterial, or to remove fluid from the region distal to the distal tip of the delivery catheter).

The delivery catheter can be is inserted into the vasculature of the patient (e.g., into the femoral vein), and advanced through the patient's vasculature, such that the distal tip of the delivery catheter reaches the patient's left atrium. The LAA may be accessed through any of a variety of pathways as will be apparent to those of skill in the art. Trans-septal access can be achieved by introducing the delivery catheter into, for example, the femoral or jugular vein, and transluminally advancing the catheter into the right atrium. Radiographic imaging (e.g., single or biplanar flouroscopy, sonographic imaging, or combinations thereof) can be used to image the delivery catheter during the procedure and guide the distal end of the catheter to the desired site. As a result, in some cases, at least a portion of the delivery catheter can be formed to be at least partially radiopaque.

Once in the right atrium, a long hollow needle with a preformed curve and a sharpened distal tip can be advanced through the auxiliary lumen, and forcibly inserted through the fossa ovalis. A radiopaque contrast media can be injected through the needle to allow visualization and ensure placement of the needle in the left atrium, as opposed to being in the pericardial space, aorta, or other undesired location. Once the position of the needle in the left atrium is confirmed, the delivery catheter can be advanced over the needle through the septum and into the left atrium. Alternative approaches to the LAA are known in the art, and can include venous transatrial approaches such as transvascular advancement through the aorta and the mitral valve.

The distal tip of the delivery catheter can then be advanced into the LAA, such that the occluding element of the delivery catheter is configured to transitorily occlude the LAA. In some cases, the occluding element is actuated to occlude the LAA. For example, in cases where the occluding element comprises an inflatable balloon configured to substantially seal the LAA when inflated, and the balloon can be inflated when the catheter is properly positioned to seal the LAA. In some embodiments, the balloon is inflated with a solution comprising a contrast agent to facilitate imaging and monitor occlusion.

If desired, fluid (e.g., blood) present in the LAA can be removed following sealing of the LAA with the occluding element. Blood can be withdrawn, for example, via the one or more auxiliary lumens. Optionally, the volume of blood removed from the LAA of the patient can be measured, and used to determine an appropriate amount of crosslinkable biomaterial to be injected into the LAA of the patient.

The crosslinkable biomaterial can then be injected into the LAA of the patient via the delivery catheter. In some embodiments, the total volume of crosslinkable biomaterial injected ranges from about 2 cc to about 8 cc. The crosslinkable biomaterial can be injected via one or more lumens, for example, using a syringe, inflator, or other device fluidly connected to the one or more lumens. In certain embodiments, the crosslinkable biomaterial can comprise a first precursor molecule present in a first solution and a second precursor molecule present in a second solution, wherein the first precursor molecule is reactive with the second precursor molecule to form a biocompatible polymeric matrix. In these embodiments, the first solution can be injected into a first lumen in the catheter and the second solution can be injected into a second lumen in the catheter. In one embodiment, the two solutions are combined during the course of injection via the delivery catheter (e.g., by mixing within a mixing channel within the delivery catheter). In another embodiment, the two solutions are individually (simultaneously or sequentially) injected into the LAA, and combine in situ to form a biocompatible polymeric matrix. In cases when the two solutions are simultaneously injected, the two solutions can be injected using, for example, a dual-barrel syringe or indeflator, wherein the first barrel contains the first solution and is fluidly connected to the first lumen, and the second barrel contains the second solution and is fluidly connected to the second lumen.

Upon injection into the LAA, the crosslinkable biomaterial increases in viscosity to form a biocompatible polymeric matrix. If desired, an accelerator (e.g., a catalyst or UV light) can be supplied to increase cure rate, initiate curing, and/or ensure thorough curing of the biocompatible polymeric matrix. The position of delivery catheter in the LAA can be maintained following injection of the crosslinkable biomaterial, such that the occluding element is configured to seal the LAA for a period of time greater than the cure time of the crosslinkable biomaterial. Following curing, the delivery catheter can be withdrawn.

In some embodiments, during the procedure described above, the patient can be positioned in a posture which is effective to facilitate occlusion of the LAA. For example, the patient can be positioned at an angle relative to the ground which is effective to facilitate injection of the crosslinkable biomaterial into the LAA of the patient. By positioning the patient at an angle (e.g., approximately a 30° to 40° angle relative to horizontal), gravity can assist the flow of the crosslinkable biomaterial into the LAA, facilitating complete occlusion of the LAA.

In general, the crosslinkable biomaterial is injected to the LAA percutaneously, for example using a delivery catheter as discussed above. Alternatively, the crosslinkable biomaterial can be introduced intraoperatively during an invasive procedure, or ancillary to another procedure which gives access to the LAA.

The methods described herein can be used to occlude the LAA, thus decreasing the risk of thromboembolic events associated with AF.

In some cases, the patient treated using the methods described herein exhibits AF. In patients with non-rheumatic AF, the risk of stroke can be estimated by calculating the patient's $CHA_2DS_2$-VASc score. A high $CHA_2DS_2$-VASc score corresponds to a greater risk of stroke, while a low $CHA_2DS_2$-VASc score corresponds to a lower risk of stroke. In some embodiments, the patient treated using the methods described has a $CHA_2DS_2$-VASc score of 2 or more.

In certain embodiments, the patient is contraindicated for anticoagulation therapy. For example, the patient can have an allergy to one or more common anticoagulants (e.g. warfarin), can express a preference to not be treated with anticoagulants, can be taking another medication that interacts unfavorably with an anticoagulant, or can be at risk for hemorrhage.

The methods, devices, and compositions described herein can be applied to occlude other cavities or passageways in a patient, in particular other cavities or passageways in the cardiovascular system of a patient. In certain embodiments, the methods, devices, and/or compositions or injected or otherwise introduced into a pseudoaneurysm to occlude the pseudoaneurysm. In certain cases, the pseudoaneurysm is present in a high risk location for surgery (e.g., connected to the aorta or another major artery). In one embodiment, the pseudoaneurysm is connected to the femoral artery.

EXAMPLES

Example 1: Synthesis and Characterization of PEG-Dextran Hydrogels

Preparation of Hydrogel Precursor Molecules

Tetra-functional PEG-thiol (PEG4SH) (82.7% activity) was purchased from Sunbio (Anyang City, South Korea), and used for hydrogel formation without further purification or modification.

Dextran from *Leuconostoc mesenteroides* (average MW=15,000-20,000 Da), divinyl sulfone (DVS; 97%, MW=118.15 Da), and 3-mercaptopropionic acid (MW=106.14 Da) were purchased from Sigma-Aldrich (St. Louis, Mo.). The synthesis of dextran vinyl sulfone (DextranVS) containing an ethyl spacer was performed using N,N0-dicyclohexyl-carbodiimide (DCC, Fisher Scientific) and 4-(dimethylamino)pyridinium 4-toluenesulfonate (DPTS) as catalysts. DPTS was prepared using methods known in the art. Briefly, 5.0 g of p-TSA monohydrate was dissolved in 100 ml THF. 4-(Dimethylamino)-pyridine (DMAP, 99%) (Sigma-Aldrich, St. Louis, Mo.) at one molar equivalent to p-TSA was added to this mixture. The mixture was subsequently filtered to isolate a precipitate which was further dissolved in dichloromethane (DCM, Fisher Scientific) and recrystallized using rotary vacuum evaporator.

Dextran vinyl sulfone ester synthesis was performed by adding 2.5 or 5.0 g DVS in 90 mL of inert nitrogen saturated DMSO, followed by dropwise addition of 3-MPA to it under continuous stirring. The reaction was continued for 4 hours in the dark. Dextran was dissolved in 30 mL DMSO, and a solution of DCC and p-TSA in 30 ml DMSO was added dropwise. The reaction mixture was stirred until a clear solution was obtained. Finally, the mixture was added to DVS/MPA solution in the dark, and reaction was allowed to proceed for 24 hours at room temperature.

After the completion of reaction, N,N-dicyclohexylurea (DCU) salt was filtered using a vacuum filter and the product was recovered by precipitation in 1000 mL of ice cold 100% ethanol. The precipitate was separated from residual ethanol through centrifugation at 3000 rpm for 15 min., followed by vacuum drying. The precipitate was re-dissolved in at least 100 mL of de-ionized water (pH adjusted to 7.8) and vortexed to obtain a clear solution. Finally, un-reacted polymer was removed via ultra-filtration using an Amicon filter (MWCO=10,000 Da, Millipore). The resulting viscous product was lyophilized to remove water. Vinyl sulfone substitution was confirmed and degree of substitution (DS) was determined via NMR spectroscopy.

Formation of PEG-Dextran Hydrogels

Controlled masses of PEG and dextran vinyl sulfone were mixed with a controlled volume of TEA buffer. Two different types of dextran vinyl sulfone (DS 5 and DS10) were examined. Samples were made with varying concentrations of hydrogel in the buffer, measured in terms of wt. %/vol. Samples ranging from 10%-40% wt./vol. were evaluated.

The PEG and dextran components were mixed in a 1:1 stoichiometric ratio.

Characterization of PEG-Dextran Hydrogels

The materials properties of the PEG-Dextran hydrogels, as well as solutions of the hydrogel precursor molecules were evaluated.

Measurement of Density and Viscosity

A controlled volume (500 µL) of each sample was collected, and weighed. Knowing the mass and volume, density was calculated. The densities measured for solutions of hydrogel precursor molecules are included in Table 1.

TABLE 1

Density measurements for solutions of hydrogel precursor molecules.
Density (g/cm³) of Materials

| | Concentration | 10% | 20% | 30% | 40% |
|---|---|---|---|---|---|
| Material | PEG | 1.080 | 1.202 | 1.295 | 1.393 |
| | Dextran DS 5 | 1.120 | 1.191 | 1.305 | 1.395 |
| | Dextran DS 10 | 1.107 | 1.193 | 1.306 | 1.399 |

Samples of hydrogel components were prepared as described previously, and heated 30 to 37° C. in a water bath. Solutions of the hydrogel precursor molecules were also measured. Kinematic viscosities were measured using size 75 and size 150 Canon Manning Semi-Micro glass capillary viscometers. Once kinematic viscosity was measured, dynamic viscosity was calculated using the following relation:

$$v = \frac{\mu}{\rho}$$

Where $v$ is kinematic viscosity, $\mu$ is dynamic viscosity, and $\rho$ is density of the measured material. For each sample, viscosity was measured 12 times to ensure accuracy. The dynamic and kinematic viscosities of solutions of hydrogel precursor molecules at different concentrations are included in Table 2.

TABLE 2

Dynamic and kinematic viscosities of solutions of hydrogel precursor molecules.

| | Concentration | 10% | 20% | 30% | 40% |
|---|---|---|---|---|---|
| | Dynamic Viscosity (cP) of Materials | | | | |
| Material | PEG | 2.646 | 7.773 | 24.729 | 32.810 |
| | Dextran DS 5 | 1.789 | 3.859 | 7.371 | 11.871 |
| | Dextran DS 10 | 1.607 | 4.075 | 6.478 | 16.335 |
| | Kinematic Viscosity (cStr) of Materials | | | | |
| Material | PEG | 2.452 | 6.467 | 19.100 | 23.556 |
| | Dextran DS 5 | 1.598 | 3.239 | 5.649 | 8.510 |
| | Dextran DS 10 | 1.451 | 3.416 | 4.960 | 11.673 |

Measurement of Degradation Rate

Samples of PEG and Dextran were mixed in a 1:1 ratio and allowed to solidify. In this study, 150 uL of each component was used. Samples were allowed to sit for two hours to allow complete solidification. To simulate human body conditions, samples were then submerged in a 0.01% PBS buffer (PH 7.4), and rotated in a 37° C. incubator. Samples were weighed at specified time intervals to gauge what percentage of material remained.

The results of the degradation trials are included in Table 3. After 90 days anywhere between 40-63% of hydrogel (by mass) had degraded. At 120 days, anywhere between 44-95% of hydrogel by mass had degraded

TABLE 3

Degradation results for PEG-dextran hydrogels.

| Day | DS 5 20% | DS 10 20% | DS 5 30% | DS 10 30% | DS 5 40% | DS 10 40% |
|---|---|---|---|---|---|---|
| | Mass/Original Mass (Swelling Ratio) | | | | | |
| 0 | 1.00 | 1.00 | 1.00 | 1.00 | 1.00 | 1.00 |
| 1 | 1.52 | 1.74 | 3.13 | 3.30 | 3.32 | 3.73 |
| 2 | 2.55 | 2.49 | 3.03 | 3.37 | 3.46 | 5.89 |
| 8 | 2.63 | 2.68 | 3.43 | 3.09 | 3.70 | 4.16 |
| 15 | 2.28 | 2.52 | 2.62 | 2.85 | 2.86 | 3.41 |
| 23 | 2.02 | 2.31 | 2.15 | 2.78 | 2.90 | 3.04 |
| 29 | 2.44 | 2.07 | 2.15 | 2.66 | 2.85 | 3.44 |
| 42 | 2.04 | 1.73 | 1.88 | 2.28 | 2.32 | 2.98 |
| 54 | 2.02 | 1.71 | 1.61 | 2.17 | 2.31 | 2.61 |
| 64 | 2.01 | 2.11 | 1.87 | 2.33 | 2.62 | 2.82 |
| 79 | 1.95 | 1.95 | 1.73 | 1.95 | 7.20 | 2.44 |
| 86 | 1.66 | 1.76 | 1.57 | 2.08 | 1.99 | 2.40 |
| 92 | 1.59 | 1.74 | 1.28 | 1.79 | 1.94 | 2.29 |
| 99 | 1.52 | 1.60 | 1.28 | 1.93 | 1.88 | 2.51 |
| 106 | 1.62 | 1.59 | 1.30 | 1.96 | 2.10 | 2.48 |
| 113 | 1.51 | 1.59 | 1.26 | 1.90 | 1.95 | 2.40 |
| 120 | 1.47 | 1.71 | 1.29 | 1.79 | 1.94 | 2.43 |
| 127 | 1.46 | 1.59 | | 1.71 | 1.92 | 2.35 |
| | % Remaining | | | | | |
| 0 | | | | | | |
| 1 | | | | | | |
| 2 | | | | 1.00 | | 1.00 |
| 8 | 1.00 | 1.00 | 1.00 | 0.92 | 1.00 | 0.71 |
| 15 | 0.87 | 0.94 | 0.76 | 0.85 | 0.77 | 0.58 |
| 23 | 0.77 | 0.86 | 0.63 | 0.83 | 0.78 | 0.57 |
| 29 | 0.93 | 0.77 | 0.63 | 0.79 | 0.77 | 0.58 |
| 42 | 0.78 | 0.64 | 0.55 | 0.68 | 0.63 | 0.51 |
| 54 | 0.77 | 0.64 | 0.47 | 0.64 | 0.62 | 0.44 |
| 64 | 0.77 | 0.79 | 0.55 | 0.69 | 0.71 | 0.48 |
| 79 | 0.74 | 0.73 | 0.50 | 0.58 | 0.59 | 0.41 |
| 86 | 0.63 | 0.66 | 0.46 | 0.62 | 0.54 | 0.41 |
| 92 | 0.61 | 0.65 | 0.37 | 0.53 | 0.52 | 0.39 |
| 99 | 0.58 | 0.60 | 0.37 | 0.57 | 0.51 | 0.43 |
| 106 | 0.62 | 0.59 | 0.38 | 0.58 | 0.57 | 0.42 |
| 113 | 0.57 | 0.59 | 0.37 | 0.56 | 0.53 | 0.41 |

TABLE 3-continued

Degradation results for PEG-dextran hydrogels.

| Day | DS 5 20% | DS 10 20% | DS 5 30% | DS 10 30% | DS 5 40% | DS 10 40% |
|---|---|---|---|---|---|---|
| 120 | 0.56 | 0.64 | 0.38 | 0.53 | 0.52 | 0.41 |
| 127 | 0.56 | 0.59 | 0.00 | 0.51 | 0.52 | 0.40 |
| % Degraded | | | | | | |
| 0 | | | | | | |
| 1 | | | | | | |
| 2 | | | | 0.00 | | 0.00 |
| 8 | 0.00 | 0.00 | 0.00 | 0.08 | 0.00 | 0.29 |
| 15 | 0.13 | 0.06 | 0.24 | 0.15 | 0.73 | 0.42 |
| 23 | 0.23 | 0.14 | 0.37 | 0.17 | 0.22 | 0.48 |
| 29 | 0.07 | 0.23 | 0.37 | 0.21 | 0.23 | 0.42 |
| 42 | 0.22 | 0.36 | 0.45 | 0.32 | 0.37 | 0.49 |
| 54 | 0.23 | 0.36 | 0.53 | 0.36 | 0.38 | 0.56 |
| 64 | 0.23 | 0.21 | 0.45 | 0.31 | 0.29 | 0.52 |
| 79 | 0.26 | 0.27 | 0.50 | 0.42 | 0.41 | 0.59 |
| 86 | 0.37 | 0.34 | 0.54 | 0.38 | 0.46 | 0.59 |
| 92 | 0.39 | 0.35 | 0.63 | 0.47 | 0.48 | 0.61 |
| 99 | 0.42 | 0.40 | 0.63 | 0.43 | 0.49 | 0.57 |
| 106 | 0.38 | 0.41 | 0.62 | 0.42 | 0.43 | 0.58 |
| 113 | 0.43 | 0.41 | 0.63 | 0.44 | 0.47 | 0.59 |
| 120 | 0.44 | 0.36 | 0.62 | 0.47 | 0.48 | 0.59 |
| 127 | 0.44 | 0.41 | 1.00 | 0.49 | 0.48 | 0.60 |

Measurement of Equilibrium Swelling Ratio

Hydrogel samples were obtained and massed. The hydrogel samples were then incubated in PBS buffer (10 mM phosphate buffered saline, e.g., P3813-powder from Sigma yields a buffer of 0.01 M phosphate, 0.0027 M potassium chloride and 0.138 M sodium chloride, pH 7.4). Upon incubation, the hydrogel samples swelled, and increased mass. Every ~168 hours (7 days), the sample was removed from buffer, and massed. The equilibrium swelling ratio, defined as:

$$\text{equilibrium swelling ratio} = \frac{w_t}{w_o}$$

where $w_t$ is the maximum swollen weight, and $w_o$ is the unswollen weight of hydrogel was determined for each hydrogel sample. Equilibrium swelling ratio was typically observe 48-72 hours after submerging samples in PBS buffer. The equilibrium swelling ratios of each hydrogel are included in Table 4 below.

TABLE 4

Equilibrium swelling ratios of PEG-dextran hydrogels.

| Dextran Component | Concentration of Hydrogel Components | | |
|---|---|---|---|
| | 20% | 30% | 40% |
| Dextran DS 5 | 2.6 | 3.4 | 3.7 |
| Dextran DS 10 | 2.6 | 3.3 | 5.8 |

Measurement of Cure Time

The cure time of the PEG-dextran hydrogels was evaluated using a tipping vial methods. PEG and Dextran suspensions were prepared, as described above, at different concentrations by mixing either PEG or dextran material with TEA buffer. Suspensions were mixed to a specific concentration. Peg and dextran suspensions of equal concentrations were then mixed in a 1:1 ratio in a sealed vial. The vial was shaken with an ultrasonic shaker to ensure complete mixing. Once mixing was complete, a timer was started. The vial was continually tipped or flipped. When mixed components stop moving upon actuation of the vial, the hydrogel is considered gelled, and the timer was stopped. All hydrogels measured exhibited curing times of 90 seconds or less.

The devices and methods of the appended claims are not limited in scope by the specific devices, systems, kits, and methods described herein, which are intended as illustrations of a few aspects of the claims. Any devices, systems, and methods that are functionally equivalent are intended to fall within the scope of the claims. Various modifications of the devices, systems, kits, and methods in addition to those shown and described herein are intended to fall within the scope of the appended claims. Further, while only certain representative devices, systems, kits, and method method steps disclosed herein are specifically described, other combinations of the devices, systems, kits, and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A kit comprising:
   (a) a delivery catheter sized to be advanced within a patient's vasculature, the delivery catheter comprising:
   a proximal region;
   a distal region comprising a distal tip;
   a first lumen extending from the proximal region to the distal region;
   an auxiliary lumen extending from the proximal region to the distal region, wherein the auxiliary lumen is fluidly isolated from the first lumen and fluidly connected to the distal tip;
   an inflatable balloon positioned in proximity to the distal tip and configured to substantially seal the LAA of the patient when inflated; and
   an inflator lumen distally extending from the proximal region and fluidly connected to the inflatable balloon;
   wherein at least a portion of the delivery catheter is formed from a material that is at least partially radiopaque
   (b) an effective amount of an injectable crosslinkable biomaterial to swell and occlude the left atrial appendage (LAA) of the patient; and
   (c) a syringe sized to accommodate the injectable crosslinkable biomaterial and deliver the injectable crosslinkable biomaterial through the delivery catheter;
   wherein the delivery catheter has a length of from about 80 cm to about 130 cm;

wherein a portion of the delivery catheter configured to be advanced within the patient's vasculature has a largest cross-sectional dimension of about 5.0 mm or less;

wherein the injectable crosslinkable biomaterial has a viscosity of about 1,000 cP or less; and wherein the crosslinkable biomaterial can crosslink in situ in the LAA of a patient to form a biocompatible polymeric matrix having a viscosity of at least 50,000 cP, an elastic modulus ranging from about 0.01 to about 100 kPa, and an equilibrium swelling ratio of from greater than 0 to about 8.

2. The kit of claim 1, wherein the delivery catheter further comprises a second lumen extending from the proximal region to the distal region, and a mixing channel positioned within the distal region of the delivery catheter fluidly connecting the first lumen and the second lumen.

3. The kit of claim 2, wherein the mixing channel comprises:
a proximal end fluidly connected to the first lumen and the second lumen;
a distal end fluidly connected to the distal tip of delivery catheter; and
a mixer fluidly connecting the proximal end and the distal end.

4. The kit of claim 1, further comprising a guidewire, sheath, or combination thereof configured to facilitate advancement of the delivery catheter within a patient's vasculature, and a hollow needle comprising a preformed curve and sharpened distal tip which is sized and configured to be advanced through the auxiliary lumen and pierce the fossa ovalis of the patient.

5. The kit of claim 1, wherein the crosslinkable biomaterial comprises a first precursor molecule and a second precursor molecule.

6. The kit of claim 5, wherein the first precursor molecule comprises an oligomer or polymer having one or more nucleophilic groups, and the second precursor molecule comprises an oligomer or polymer having one or more conjugated unsaturated groups.

7. The method of claim 6, wherein the first precursor molecule comprises a poly(alkylene oxide)-based oligomer or polymer having x nucleophilic groups, wherein x is an integer of from 2 to 6.

8. The kit of claim 7, wherein the first precursor molecule comprises pentaerythritol poly(ethylene glycol)ether tetra-sulfhydryl.

9. The kit of claim 6, wherein the second precursor molecule comprises a biomacromolecule having y conjugated unsaturated groups, wherein y is an integer of from 2 to 25.

10. The kit of claim 9, wherein the second precursor molecule comprises dextran vinyl sulfone.

11. The kit of claim 1, wherein the crosslinkable biomaterial has a cure time of less than about 20 minutes.

12. The kit of claim 1, wherein the biocompatible polymeric matrix has a degradation rate such that about 70% or less by weight of the biocompatible polymeric matrix degrades within 90 days of curing.

13. The kit of claim 1, wherein the biocompatible polymeric matrix exhibits an equilibrium swelling ratio of from about 2 to about 8.

14. The kit of claim 1, wherein the biocompatible polymeric matrix has an elastic modulus of from about 8 kPa to about 12 kPa.

15. The kit of claim 1, wherein the biocompatible polymeric matrix reaches equilibrium swelling within about 24 hours.

16. The kit of claim 1, wherein the effective amount of crosslinkable biomaterial comprises from about 2 cc to about 8 cc.

17. The kit of claim 1, wherein the biocompatible polymeric matrix is not biodegradable.

18. The kit of claim 1, wherein the inflatable balloon has a cross-sectional dimension of at least about 1.0 cm when inflated.

19. The kit of claim 1, wherein the delivery catheter further comprises a manifold configured to facilitate access to the first lumen, the auxiliary lumen, and the inflator lumen.

20. The kit of claim 1, wherein the inflatable balloon is positioned within about 10 mm the distal tip.

* * * * *